US 9,426,585 B2

(12) United States Patent
Thiede

(10) Patent No.: US 9,426,585 B2
(45) Date of Patent: Aug. 23, 2016

(54) BINAURAL HEARING AID SYSTEM AND A METHOD OF PROVIDING BINAURAL BEATS

(71) Applicant: Widex A/S, Lynge (DK)

(72) Inventor: Thilo Volker Thiede, Copenhagen Ø (DK)

(73) Assignee: Widex A/S, Lynge (DK)

( * ) Notice: Subject to any disclaimer, the term of this patent is extended or adjusted under 35 U.S.C. 154(b) by 419 days.

(21) Appl. No.: 13/834,105

(22) Filed: Mar. 15, 2013

(65) Prior Publication Data

US 2013/0202119 A1    Aug. 8, 2013

Related U.S. Application Data

(63) Continuation-in-part of application No. PCT/EP2011/051457, filed on Feb. 2, 2011.

(51) Int. Cl.
*H04R 25/00* (2006.01)
*A61B 5/0482* (2006.01)
*A61B 5/00* (2006.01)

(52) U.S. Cl.
CPC .............. *H04R 25/50* (2013.01); *A61B 5/0482* (2013.01); *H04R 25/552* (2013.01); *H04R 25/75* (2013.01); *A61B 5/6815* (2013.01)

(58) Field of Classification Search
None
See application file for complete search history.

(56) References Cited

U.S. PATENT DOCUMENTS

| 5,135,468 | A | * | 8/1992 | Meissner | A61M 21/00 |
| | | | | | 600/28 |
| 5,748,751 | A | * | 5/1998 | Janse et al. | 381/93 |
| 6,816,599 | B2 | | 11/2004 | Thiede et al. | |
| 7,769,439 | B2 | * | 8/2010 | Vesely et al. | 600/544 |
| 8,031,892 | B2 | | 10/2011 | Andersen et al. | |
| 2004/0208332 | A1 | | 10/2004 | Baechler | |
| 2011/0046435 | A1 | * | 2/2011 | Jensen et al. | 600/28 |

FOREIGN PATENT DOCUMENTS

| WO | 99/43185 A1 | 8/1999 |
| WO | WO 9943185 A1 * | 8/1999 |
| WO | 2006/101571 A2 | 9/2006 |
| WO | 2009/054699 A1 | 4/2009 |
| WO | 2011/006681 A1 | 1/2010 |

OTHER PUBLICATIONS

S. Wardle, "A Hilbert-Transformer Frequency Shifter for Audio", Proc. DAFX98 Workshio on Digital Audio Effects, pp. 1, Barcelona 1998.*
D. W. Schwarz et al, "Human auditory steady state responses to binaural and monaural beats", Clinical Neurophysiology, Elsevier Science, IE, vol. 116, No. 3, Mar. 1, 2005, pp. 658-668 XP004766641.
James R. Lackner et al, "The auditory characteristics of tinnitus resulting from cerebral injury", Experimental Neurology, Academic Press, New York, NY, US, vol. 51, No. 1, Jan. 1, 1976, pp. 54-67, XP026257283.

(Continued)

*Primary Examiner* — Jesse Elbin
*Assistant Examiner* — Kenny Truong
(74) *Attorney, Agent, or Firm* — Sughrue Mion, PLLC

(57) ABSTRACT

A binaural hearing aid system (100) is adapted to provide binaural beats to a hearing aid user. The invention further provides a method of generating binaural beats.

20 Claims, 4 Drawing Sheets

(56) References Cited

OTHER PUBLICATIONS

International Search Report for PCT/EP2011/051457 dated Sep. 23, 2011.

Written Opinion of the International Preliminary Examining Authority for PCT/EP2011/051457 dated Jan. 15, 2013.

\* cited by examiner

BINAURAL HEARING AID SYSTEM AND A METHOD OF PROVIDING BINAURAL BEATS

RELATED APPLICATIONS

The present application is a continuation-in-part of application PCT/EP2011051457, filed on 2 Feb. 2011, in Europe, and published as WO2012103940 A1.

BACKGROUND OF THE INVENTION

1. Field of the Invention

The present invention relates to hearing aid systems. The invention more specifically relates to binaural hearing aid systems, configured to provide binaural beats. The invention also relates to a method of providing binaural beats.

In the context of the present disclosure, a hearing aid should be understood as a small, microelectronic device designed to be worn behind or in a human ear of a hearing-impaired user. A hearing aid system may be monaural and comprise only one hearing aid or be binaural and comprise two hearing aids. Prior to use, the hearing aid is adjusted by a hearing aid fitter according to a prescription. The prescription is based on a hearing test, resulting in a so-called audiogram, of the performance of the hearing-impaired user's unaided hearing. The prescription is developed to reach a setting where the hearing aid will alleviate a hearing loss by amplifying sound at frequencies in those parts of the audible frequency range where the user suffers a hearing deficit. A hearing aid comprises one or more microphones, a microelectronic circuit comprising a signal processor, and an acoustic output transducer. The signal processor is preferably a digital signal processor. The hearing aid is enclosed in a casing suitable for fitting behind or in a human ear.

As the name suggests, Behind-The-Ear (BTE) hearing aids are worn behind the ear. To be more precise an electronics unit comprising a housing containing the major electronics parts thereof, is worn behind the ear. An earpiece for emitting sound to the hearing aid user is worn in the ear, e.g. in the concha or the ear canal. In a traditional BTE hearing aid, a sound tube is used because the output transducer, which in hearing aid terminology is normally referred to as the receiver, is located in the housing of the electronics unit. In some modern types of hearing aids a conducting member comprising electrical conductors is used, because the receiver is placed in the earpiece in the ear. Such hearing aids are commonly referred to as Receiver-In-The-Ear (RITE) hearing aids. In a specific type of RITE hearing aids the receiver is placed inside the ear canal. This is known as Receiver-In-Canal (RIC) hearing aids.

In-The-Ear (ITE) hearing aids are designed for arrangement in the ear, normally in the funnel-shaped outer part of the ear canal. In a specific type of ITE hearing aids the hearing aid is placed substantially inside the ear canal. This type is known as Completely-In-Canal (CIC) hearing aids. This type of hearing aid requires a very compact design in order to allow it to be arranged in the ear canal, while accommodating the components necessary for operation of the hearing aid, such as microphones, a microelectronic circuit comprising a signal processor, an acoustic output transducer and a battery.

Binaural beats are auditory brainstem responses which originate in the superior olivary nucleus of each hemisphere. They result from the interaction of two different auditory impulses, originating in opposite ears and which differ in frequency between say one and 30 Hz. For example, if a pure tone of 400 Hz is presented to the right ear and a pure tone of 410 Hz is presented simultaneously to the left ear, using stereo headphones, an amplitude modulated wave of 10 Hz, the difference between the two tones, is experienced as the two wave forms mesh in and out of phase within the superior olivary nuclei. This binaural beat is not heard in the ordinary sense of the word (the human range of hearing is from 20-20,000 Hz). It is perceived as an auditory beat and can be used to entrain specific neural rhythms through the frequency-following response (FFR)—the tendency for cortical potentials to entrain to or resonate at the frequency of an external stimulus. Thus, it is possible to utilize a specific binaural-beat frequency as a consciousness management technique to entrain a specific cortical rhythm.

Binaural beats reportedly influence the brain in more subtle ways through the entrainment of brainwaves and can be used to reduce anxiety and provide other health benefits such as control over pain.

The binaural-beat appears to be associated with an electroencephalographic (EEG) frequency-following response in the brain. Many studies have demonstrated the presence of a frequency-following response to auditory stimuli, recorded at the vertex of the human brain (top of the head). This EEG activity was termed "frequency-following response" because its period corresponds to the fundamental frequency of the stimulus. The concept is that if one receives a stimulus with a frequency in the range of brain waves, the predominant brain wave frequency is said to be likely to move towards the frequency of the stimulus (a process called entrainment).

The subjective effect of listening to binaural beats may be relaxing or stimulating, depending on the frequency of the binaural-beat stimulation.

Binaural beats in the delta (1 to 4 Hz) and theta (4 to 8 Hz) ranges have been associated with relaxed, meditative, and creative states and used as an aid to falling asleep.

Binaural beats in the alpha frequencies (8 to 12 Hz) have increased alpha brain waves that have been associated with relaxation while awake, and binaural beats in the beta frequencies (typically 16 to 24 Hz) have been associated with reports of increased concentration or alertness.

When the perceived beat frequency corresponds to the delta, theta, alpha, beta, or gamma range of brainwave frequencies, the brainwaves entrain to or move towards the beat frequency.

Binaural beat stimulation has been used fairly extensively to induce a variety of states of consciousness, and there has been some work done in regards to the effects of these stimuli on relaxation, focus, attention, and states of consciousness. Studies have shown that a plastic reorganization of the brain occurs with repeated training to distinguish sounds that only exhibit minor frequency deviations.

The dominant frequency determines your current state. For example, if in someone's brain alpha waves are dominating, it is in the alpha state (this happens when one is relaxed but awake). However, also other frequencies will be present, albeit with smaller amplitudes.

2. The Prior Art

U.S. Pat. No. 6816599 B2 provides a method for synthesizing music, using a pseudo-random generator.

WO-A1-2011/006,681 provides a system for brain wave measurement. U.S. Pat. No. 8,031,892 B2 provides a hearing aid with means for shifting a signal in frequency.

It has been suggested that binaural beats can be advantageous as part of Tinnitus Retraining Theraphy (TRT). However, some experiments suggest that TRT may require about 18 months achieving observable stable effects. This kind of TRT therefore requires a considerable amount of patience and discipline from the patient.

The brain wave entraining is more effective if the entraining frequency is close to the user's starting dominant frequency. Therefore, it is suggested to start with a frequency near to one's current dominant frequency (likely to be about 20 Hz or less for a waking person), and then slowly decreasing it towards the desired frequency.

It has been suggested to induce binaural beats by providing sounds for the user that have been specially recorded and stored on some form of audio media. The sounds can be provided using headphones.

One problem with these prior art systems is that they do not encourage the user to frequent and long term training sessions, because the systems are inflexible insofar as the patient, as part of the training, can only listen to the sounds that have been specially recorded and stored on some audio media. This will typically be problematic since the user most likely will perceive it as quite boring to listen again and again to the same specially recorded sounds.

Another problem arises if the audio media is lost, damaged or for some reason not brought along by the patient.

Still another problem with the prior art is that the user's dominant brain frequency is not known at the initiation of the training, and the effectiveness of the training can therefore not be optimized by fine tuning the frequency of the induced binaural beats.

A further problem is that even if the dominant brain frequency was known it is not possible to fine tune the binaural beats in the training session to take this information into account, because the user only has to his disposal prerecorded sounds on some form of audio media.

It is therefore a feature of the present invention to provide a hearing aid system with improved means for providing binaural beats for the hearing aid user.

It is another feature of the present invention to provide an improved method for providing binaural beats.

SUMMARY OF THE INVENTION

The invention, in a first aspect, provides a binaural hearing aid system comprising a first hearing aid, a second hearing aid, wireless link means and synchronizing means, wherein said first hearing aid comprises a first acoustical-electrical transducer for transforming an acoustic signal into a first audio input signal; a first processing means configured to amplify a first processor input signal and provide a first processor output signal; a first electrical-acoustical output transducer adapted for converting the processor output signal into sound; first sound generating means adapted for providing a first synthesized signal; first frequency shift means adapted for shifting a first electrical audio signal in frequency hereby providing a first frequency-shifted electrical audio signal, wherein said first electrical audio signal is one of said first audio input signal and said first synthesized signal; first summing means adapted for adding the first frequency-shifted electrical audio signal to the other one of said first audio input signal and said first synthesized signal to provide said first processor input signal; wherein the wireless link means is configured for establishing a wireless connection between said first and said second hearing aid of the binaural hearing aid system; and wherein the synchronizing means is adapted for synchronizing the operation of said first hearing aid and said second hearing aid at least with respect to said first frequency-shifted electrical audio signal.

This provides a hearing aid with improved means for providing binaural beats for the hearing aid user.

The invention, in a second aspect, provides a method of providing binaural beats comprising the steps of providing a first electronic device and a second electronic device adapted for wearing at respective ears of a user; generating a first electrical audio signal in the first electronic device and a second electrical audio signal in the second electronic device; synchronizing said first electrical audio signal with said second electrical audio signal; and frequency shifting said first electrical audio signal by a fixed frequency relative to the second electrical audio signal and selected to provide a binaural beat; wherein said step of generating said first and second electrical audio signals comprises the steps of generating a pseudo-random number, calculating parameters of a tone from a generated pseudo-random number, generating an electrical audio signal according to the calculated parameters and controlling said generation of the electrical audio signal by using control parameters calculated from a generated pseudo-random number.

This provides an improved method for inducing binaural beats.

Further advantageous features appear from the dependent claims.

Still other features of the present invention will become apparent to those skilled in the art from the following description wherein the invention will be explained in greater detail.

BRIEF DESCRIPTION OF THE DRAWINGS

By way of example, there is shown and described a preferred embodiment of this invention. As will be realized, the invention is capable of other embodiments, and its several details are capable of modification in various, obvious aspects all without departing from the invention. Accordingly, the drawings and descriptions will be regarded as illustrative in nature and not as restrictive. In the drawings.

DETAILED DESCRIPTION

Figure 1:
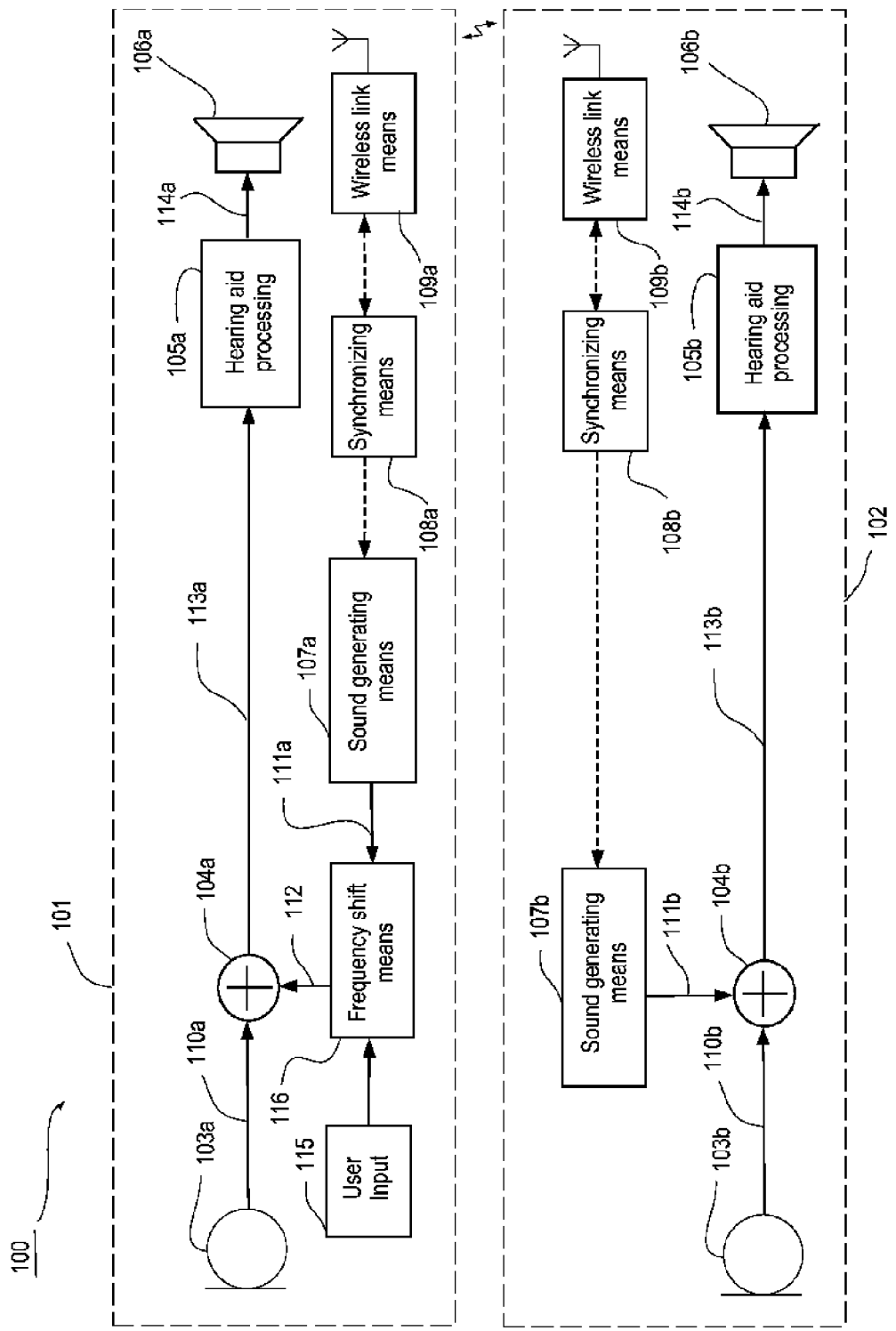
FIG. 1 illustrates highly schematically a hearing aid system according to an embodiment of the invention.

Reference is now made to FIG. 1, which illustrates highly schematically a hearing aid system 100 according to an embodiment of the invention. The hearing aid system 100 comprises a first hearing aid 101 and a second hearing aid 102. The first hearing aid 101 comprises an acoustical-electrical transducer 103*a*, a summing unit 104*a*, a hearing aid signal processor 105*a*, an electrical-acoustical transducer 106*a*, sound generating means 107*a*, frequency shift means 116, synchronizing means 108*a*, wireless link means 109*a* and user input means 115.

In the first hearing aid 101 the acoustical-electrical transducer 103*a* transforms an acoustic signal from the surroundings into a first electrical audio signal 110*a*, which is provided to a first input of the summing unit 104*a*. The sound generating means 107*a* synthesizes and provides a second electrical audio signal 111*a* to the frequency shift means 116 that transforms the second electrical audio signal into a frequency shifted electrical audio signal 112, which is provided to a second input of the summing unit 104*a*. The summing unit 104*a* provides a sum signal 113*a* that is the sum of the first electrical audio signal 110*a* and the frequency shifted electrical audio signal 112. The sum signal 113a is provided to an input of the hearing aid processor 105a for further standard hearing aid signal processing adapted for alleviating a hearing deficit of the hearing aid user. The hearing aid processor 105a provides an electrical output signal 114a to the electrical-acoustical transducer 106a for converting the electrical output signal 114a into sound. The synchronizing means 108a ensures that the sound generating means 107a is synchronized in time and with respect to frequency content with the contra-lateral sound generating means 107b. The synchronization is achieved by exchanging status data between the two hearing aids 101, 102 using the wireless link means 109a and 109b. The user input means 115 allows the user to control the frequency shift means 116 whereby binaural beats with various characteristics can be obtained.

The second hearing aid 102 functions similar to the first hearing aid 101 apart from the fact that the frequency shift means 116 and user input means 115 are not part of the second hearing aid 102 and consequently that the electrical audio signal 111b provided by the sound generating means 107b are fed directly to a second input of the summing unit 104b.

According to a variation of the embodiment of FIG. 1, the first and second hearing aids are substantially identical. Hereby the desired binaural beat frequency can be provided by using the frequency shift means in both hearing aids to frequency shift the electrical audio signals, with a frequency corresponding to half the binaural beat frequency, in opposite directions—i.e. frequency shifting towards lower frequencies in the first hearing and towards higher frequencies in the second hearing aid or vice versa. It is a specific advantage of this variation that the produced audio signal will sound less distorted and that any relative time delay that may be introduced by the frequency shift means is no longer an issue.

According to another variation of the embodiment of FIG. 1 two or more of the digital processing units 105a, 105b, 107a, 107b, 108a, 108b and 116 may be integrated in a digital signal processor in each of the respective hearing aids 101 and 102.

According to another variation of the embodiment of FIG. 1 the summing unit 104a is positioned downstream of the hearing aid processor 105a.

Figure 2:
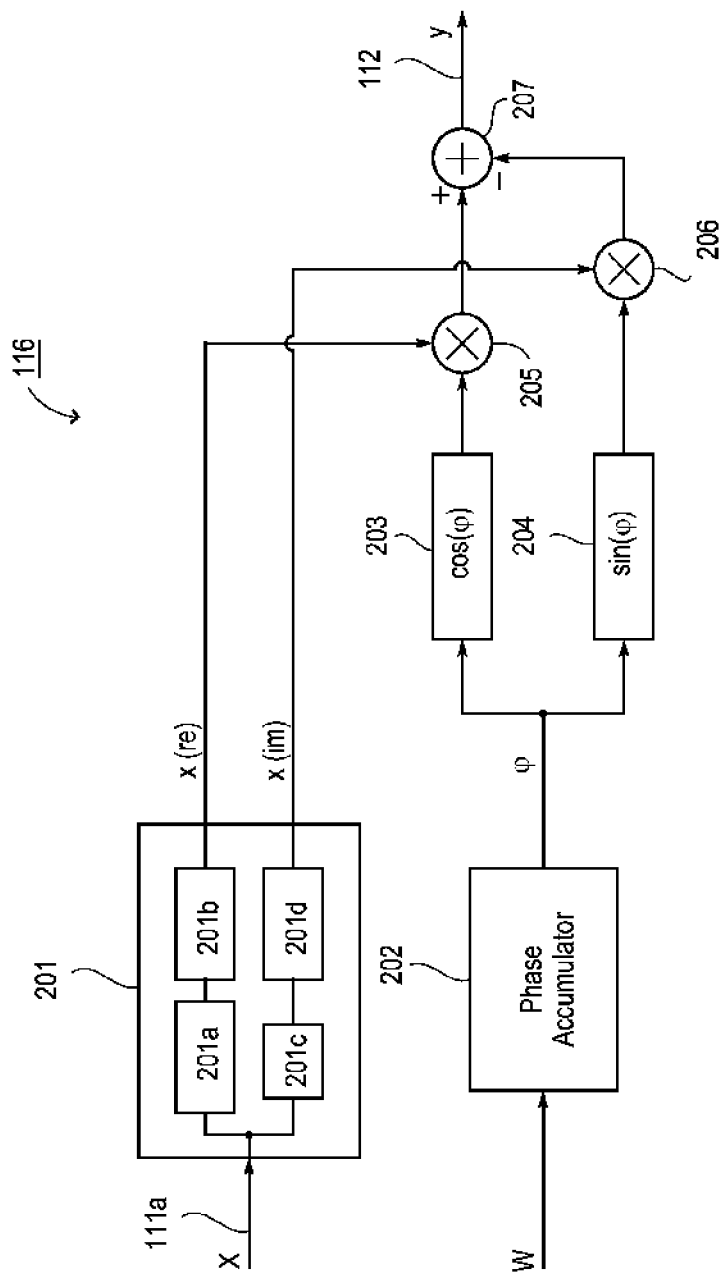
FIG. 2 shows a block schematic of the frequency shift means according to an embodiment the invention.

Reference is now given to FIG. 2 that shows a block schematic of the frequency shift means 116 according to an embodiment the invention. The frequency shift means 116 comprises a Hilbert transformer 201, a phase accumulator 202, a cosine function block 203, a sine function block 204, a first multiplier node 205, a second multiplier node 206 and a difference node 207. The Hilbert transformer 201 comprises a first all-pass filter 201a, a second all-pass filter 201b, a phase inverter 201c and a third all-pass filter 201d. The frequency shift means 116 accepts as first input a source signal X (corresponding to the second electrical audio signal 111a described above with reference to FIG. 1) and as a second input a transposing frequency W, that is the frequency of the binaural beat to be provided by the system and that in the embodiment according to FIG. 1 is provided by the user input 115. The frequency shift means 116 then as a result outputs a signal y that corresponds to the frequency shifted electrical audio signal 112 described above with reference to FIG. 1.

The signal to be frequency-shifted enters the Hilbert transformer 201 of the frequency shift means 116 as the input signal X. In the Hilbert transformer 201, the signal X is split up into two branches. The first branch, comprising the first all-pass filter 201a and the second all-pass filter 201b, isolates the real part $x_{re}$ of the signal X, and the second branch, comprising the phase inverter 201c and the third all-pass filter 201b, isolates the imaginary part $x_{im}$ of the signal X. The net result of this operation on the signal X is that the imaginary signal part $x_{im}$ is phase-shifted −90° relative to the real signal part $x_{re}$.

The real signal part $x_{re}$ is fed to the first multiplier node 205, and the imaginary signal part $x_{im}$ is fed to the second multiplier node 206.

The frequency W is fed to the phase accumulator 202 for generating a phase signal $\phi$. The phase signal $\phi$ is split into two branches and fed to the cosine function block 203 and the sine function block 204, respectively, for generating the cosine and the sine of the phase signal $\phi$, respectively. The real signal part $x_{re}$ is multiplied with the cosine of the phase signal $\phi$ in the first multiplier node 205, and the imaginary signal part $x_{im}$ is multiplied with the sine of the phase signal y in the second multiplier node 206.

In the difference node 207 of the frequency shift means 116, the output signal from the second multiplier node 206, carrying the product of the imaginary signal part $x_{im}$ and the sine of the phase signal $\phi$, is subtracted from the output signal from the first multiplier node 205 carrying the product of the real signal part $x_{re}$ and the cosine of the phase signal $\phi$, producing the frequency-shifted output signal y that has been frequency-shifted by the value of W.

It is particularly advantageous to use a method for frequency shifting based on a Hilbert transform in a hearing aid, because the Hilbert transform can be used for other purposes in a hearing aid, such as speech detection and frequency transposition.

In the embodiment according to FIG. 1 the sound generating means 107a and 107b provide an electrical audio signal that is relaxing and comfortable to listen to. In this embodiment the sound generating means 107a and 107b are implemented in accordance with the methods for music synthesizing described in U.S. Pat. No. 6816599B2. Herein is described a music synthesizer that corresponds to the sound generating means 107a and 107b.

The music synthesizer comprises a set of sound generators that are controlled digitally. Each sound generator is adapted to generate an electronic signal representing a tone of a specific loudness and frequency and with a specific spectral content, thus, representing a tone with a specific sonorous figure. Further, fade-in and fade-out time constants of a generated tone are controlled. The adjustable parameters, such as loudness, frequency, spectral content, fade-in, fade-out and tone duration, of the sound generators are controlled digitally by a controller included in the music synthesizer.

The controller comprises a pseudo-random number generator for generation of sequences of pseudo-random numbers. A parameter of a sound generator is determined based on the value of the number generated by the pseudo-random number generator. In a pseudo-random number sequence, the next number can't be determined from the previous number or a short sequence of the previous numbers if the initial conditions of the number sequence are not known. The controller further comprises a temporal generator comprising a pseudo-random generator for determination of time periods between start of generation of successive tones. The pseudo-random number generator is adapted to generate a sequence of self-similar numbers. It is an important advantage that synthesizing music with a pseudo-random number generator eliminates a need for a large memory capable of storing a selection of recorded music sufficiently large for the user not to be upset with repeated listening to the same music. For example, carrying a separate device with larger capacity and thus a broader selection of music would in general be considered cumbersome and incompatible with the daily use.

It has further been shown that music synthesized utilizing a pseudo-random number generator generating self-similar numbers is surprisingly relaxing and comfortable to listen to. Further, a music sequence generated by such a number generator is extremely long so that a person listening to the music does not perceive listening to repeated music sequences. Thus, by synthesizing music in this way it is achieved that the synthesized music is perceived to be virtually non-repetitive, i.e. a listener does not recognize a repeated sequence. It is a further advantage that the music synthesizer can conveniently be accommodated in a hearing aid or in a hearing aid type of housing to be worn behind the ear, in the ear, or in the ear canal, without a need for a remote unit for storage and transmission of music to the hearing aid or the hearing aid type of housing.

According to the embodiment of FIG. 1, the sound generators 107a and 107b are synchronized by copying the content of the status registers comprising the result of the pseudo number generator from the first hearing aid 101 and to the second hearing aid 102.

It is a specific advantage of the invention according to the embodiment of FIG. 1 that the hearing aid user can select between a wide range of binaural beat frequencies (i.e. the value of the frequency shift), through the user input means 115.

Additionally the user input means 115 allows the hearing aid user to select between a plurality of electrical audio signals as will be further described below with reference to FIG. 3.

According to a variation of the embodiment of FIG. 1 the value of the frequency shift (i.e. the binaural beat frequency) is selected automatically by the hearing aid based on e.g. a classification of the sound environment or based on a brain wave measurement as will be further described below with reference to FIG. 4.

The user input means 115 may comprise a handle or push-button accommodated on the hearing aid, or the user input means 115 can be configured to communicate wirelessly with an external device.

According to variations of the embodiment of FIG. 1 the hearing aid or the external device can present relevant information in order to assist the hearing aid user in selecting the most appropriate binaural beat frequency for a given situation. E.g. whether the hearing aid user intends to relax or whether the user needs to increase his concentration or alertness.

Figure 3:
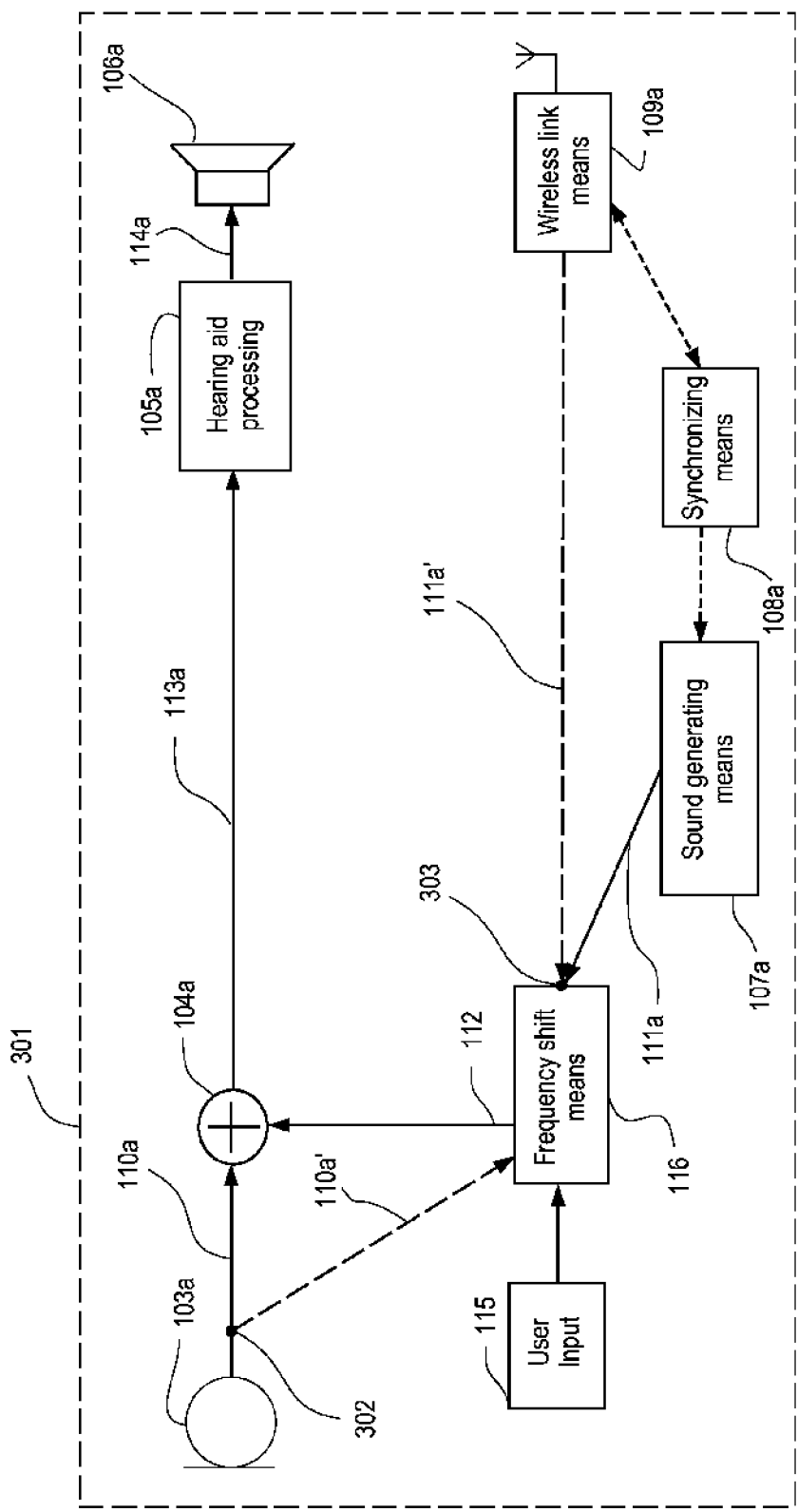
FIG. 3 illustrates highly schematically a first hearing aid of a hearing aid system according to an embodiment of the invention.

Reference is now made to FIG. 3 that illustrates highly schematically a first hearing aid 301 of a hearing aid system according to an embodiment of the invention. The hearing aid 301 comprises all of the components of the first hearing aid 101 described above with reference to FIG. 1 and additionally comprises first and second switching means 302 and 303.

The first switching means 302 is adapted such that the electrical audio signal 110a, 110a' provided by the acoustical-electrical transducer 103a is either fed to the first input of the summing unit 104a or is alternatively fed to the frequency shift means 116 and further on to the second input of the summing unit 104a. In the latter case it hereby becomes possible to increase alertness and hence speech intelligibility for the hearing aid user in daily life situations by including a binaural beat in the ambient sound provided to the hearing aid user.

The second switching means 303 is adapted such that in a first case the sound generating means 107a synthesizes and provides an electrical audio signal 111a to the frequency shift means 116. This corresponds to the situation that has already been described above with reference to FIG. 1. In a second case an electrical audio signal 111a' is provided, from the wireless link means, to the frequency shift means 116 and further on to the second input of the summing unit 104a. In this way the electrical audio signal 111a', provided by the wireless link means 109a, which is assumed to be identical in the two hearing aids, provides a binaural beat. The streamed electrical audio signal 111a' may represent any type of audio signals such as e.g. music streamed from a mobile phone, personal computer or any other suitable music player or it may represent speech received from a telecoil or FM system.

Hereby the hearing aid user is not limited in his choice of music if the user desires to enjoy the benefit of the binaural beats, because special music recordings capable of providing a binaural beat are no longer required in order to enjoy the benefit of the binaural beats.

According to a variation of the embodiment of FIG. 3 the electrical audio signal 110a, 110a', 111a, 111a' to be frequency shifted is selected automatically by the hearing aid based on e.g. a classification of the sound environment or based on a predetermined hierarchy of the available electrical audio signals.

According to a variation of the embodiments of FIG. 1 and FIG. 2, the frequency shift means 116 is adapted such that a frequency shift is only applied to a given range of frequency components of the electrical audio signal 110a, 110a', 111a and 111a'. According to a further variation this frequency range only include frequency components below 1500 Hz or only frequency components below 1000 Hz.

Figure 4:
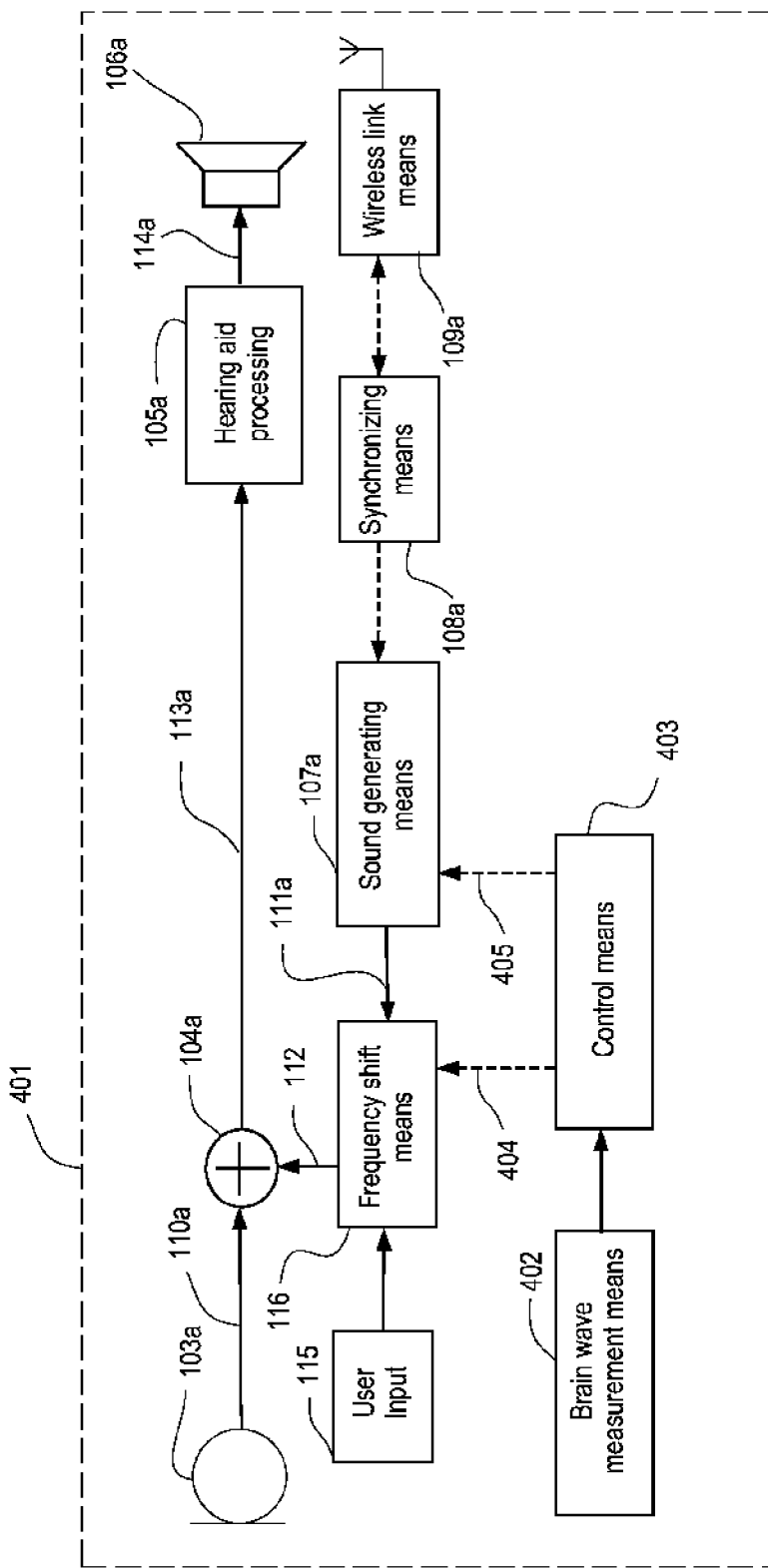
FIG. 4 illustrates highly schematically a first hearing aid of a hearing aid system according to another embodiment of the invention.

Reference is now made to FIG. 4 that illustrates highly schematically a first hearing aid 401 of a hearing aid system according to an embodiment of the invention. The hearing aid 401 comprises all of the components of the first hearing aid 101 described above with reference to FIG. 1 and additionally comprises brain wave measurement means 402 and control means 403 adapted to control the frequency shift means 116 and the sound generating means 107a using frequency shift control signals 404 and sound generating control signals 405. The measured brain waves are fed to the control means 403, where the brain waves are analyzed, and the frequency shift means 116 and sound generating means 107a are controlled accordingly in dependence on this analysis.

Further details concerning a hearing aid system with brain wave measurement means can be found in e.g. patent application PCT/EP2010/051005, published as WO-A1-2011/006681.

According to a variation of the embodiment of FIG. 4 the brain wave measurement means 402 comprises at least two surface electrodes integrated in an earpiece part of a hearing aid.

According to a variation of the embodiment of FIG. 4 the measured brain waves are used to determine whether a state of mind corresponding to the selected characteristics of the binaural beat has in fact been induced.

If the desired state of mind has not been induced sufficiently, the binaural hearing aid system can try to improve the situation by:
    automatically vary the selected binaural beat frequency,
    automatically vary the general sound characteristics, such as e.g. frequency content and loudness, of the electrical audio signal used to provide the binaural beat,
    issue a warning using the sound generating means, and encourage the hearing aid user to manually change the above mentioned characteristics,
    suggest to use another type of electrical audio signal, e.g. the internally generated sounds described with reference to FIG. 1, instead of wireless streaming of non-synthesized music as described with reference to FIG. 3, or vice versa.

According to yet another variation of the embodiment of FIG. 4 the brain wave measurement means 402 is used to select the initial binaural beat frequency based on a brain wave measurement determining the dominant brain wave frequency within the binaural beat frequency range corresponding to the desired state of mind.

According to yet another variation of the embodiment of FIG. 4 the brain wave measurement means 402 is configured such that the brain waves are measured in or at the left ear and the right ear of the hearing aid user. In case a significant unbalance is measured, the control means 403 is adapted to control the frequency shift means 116 such that the value of the frequency shift and hence the binaural beat corresponds to the brain wave frequency where the unbalance has been detected.

The invention claimed is:

1. A binaural hearing aid system comprising a first hearing aid, a second hearing aid, a wireless link component and a synchronizer,
    wherein said first hearing aid comprises
       a first acoustical-electrical transducer for transforming an acoustic signal into a first audio input signal;
       a first processor configured to amplify a first processor input signal and provide a first processor output signal;
       a first electrical-acoustical output transducer adapted for converting the processor output signal into sound;
       a first sound generator adapted for providing a first synthesized signal;
       a first frequency shifter adapted for shifting a first electrical audio signal in frequency hereby providing a first frequency-shifted electrical audio signal, wherein said first electrical audio signal is one of said first audio input signal and said first synthesized signal;
       a first summer adapted for adding the first frequency-shifted electrical audio signal to the other one of said first audio input signal and said first synthesized signal to provide said first processor input signal;
    wherein the
    wireless link component is configured for establishing a wireless connection between said first and said second hearing aid of the binaural hearing aid system; and
    wherein the
    synchronizer is adapted for synchronizing the operation of said first hearing aid and said second hearing aid at least with respect to said first frequency-shifted electrical audio signal.

2. The binaural hearing aid system according to claim 1, wherein said first sound generator is arranged in said first hearing aid.

3. The binaural hearing aid system according to claim 1, comprising an external device having a synthesized signal generator, wherein said first sound generator receives the first synthesized signal from said external device by said wireless link component and provides said first synthesized signal to one of said first frequency shifter and first summer.

4. The binaural hearing aid system according to claim 1, wherein said first hearing aid comprises a switch operable for selectively directing the output signal from said first acoustical-electrical transducer to said first frequency shifter.

5. The binaural hearing aid system according to claim 1, wherein said frequency shifter is adapted to provide a binaural beat frequency in the range between 0.5 and 40 Hz.

6. The binaural hearing aid system according to claim 1, wherein said second hearing aid comprises
    a second acoustical-electrical transducer for transforming an acoustic signal into a second audio input signal;
    a second processor configured to amplify a second processor input signal and provide a second processor output signal;
    a second electrical-acoustical output transducer adapted to convert the second processor output signal into sound;
    second sound generator adapted for providing a second synthesized signal;
    second frequency shifter adapted for shifting a second electrical audio signal in frequency hereby providing a second frequency-shifted electrical audio signal, wherein said second electrical audio signal is one of said second audio input signal and said second synthesized signal; and
    a second summer adapted for adding the second frequency-shifted electrical audio signal to the other one of said second audio input signal and said second synthesized signal to provide said second processor input signal;
    whereby said first frequency shifter and said second frequency shifter are adapted for shifting the electrical audio signal in the respective hearing aids in opposite directions and with values that together provide the desired binaural beat frequency.

7. The binaural hearing aid system according to claim 1, wherein said first frequency shifter is adapted to apply a fixed frequency shift to the frequency components of the electrical audio signal within a predetermined frequency range.

8. The binaural hearing aid system according to claim 7, wherein said frequency range comprises frequency components below 1500 Hz.

9. The binaural hearing aid system according to claim 6, wherein said first and said second sound generators comprises a pseudo-random number generator for generating a pseudo-random number, a parameter calculator for calculating parameters of a tone from the generated random number, and a further sound generator for generating an electric signal according to the calculated parameters.

10. The binaural hearing aid system according to claim 9, wherein each of said first and said second sound generators comprises a set of sound generators and a controller for controlling the set of sound generators, and wherein control parameters of the set of sound generators are calculated by the controller from numbers generated by the pseudo-random number generator.

11. The binaural hearing aid system according to claim 1, wherein each of said first and said second frequency shifters comprises a Hilbert transformer, and wherein single sideband modulation is used to provide the frequency shift.

12. The binaural hearing aid system according to claim 1, comprising a user interface adapted for enabling selection of the value of said binaural beat frequency.

13. The binaural hearing aid system according to claim 1, comprising a brain wave measurement component.

14. The binaural hearing aid system according to claim 13, comprising a controller adapted to select at least one of the binaural beat frequency and the loudness of the audio output in dependence on a measured brain wave.

15. The binaural hearing aid system according to claim 1, wherein said first sound generator generates said first synthesized signal independently of said first audio input signal.

16. A method of providing binaural beats comprising the steps of:
    providing a first electronic device and a second electronic device adapted for wearing at respective ears of a user;

generating a first electrical audio signal in the first electronic device and a second electrical audio signal in the second electronic device;
synchronizing said first electrical audio signal with said second electrical audio signal; and
frequency shifting said first electrical audio signal by a fixed frequency relative to the second electrical audio signal and selected to provide a binaural beat;
wherein said step of generating said first and second electrical audio signals comprises the steps of:
generating a pseudo-random number, calculating parameters of a tone from a generated pseudo-random number, generating an electrical audio signal according to the calculated parameters and controlling said generation of the electrical audio signal by using control parameters calculated from a generated pseudo-random number.

17. The method according to claim 16, wherein said step of frequency shifting said first electrical audio signal comprises a step of Hilbert transforming said first electrical audio signal.

18. The method according to claim 16, comprising the step of measuring a brain wave of a user wearing said first and second electronic device.

19. The method according to claim 18, comprising the step of selecting the value of the binaural beat frequency in dependence on a measured brain wave.

20. The method according to claim 18, comprising the step of selecting the value of the binaural beat frequency in dependence on an unbalance between the brain waves measured at the left and the right ear.

* * * * *